United States Patent [19]

Noon et al.

[11] Patent Number: 4,573,883

[45] Date of Patent: Mar. 4, 1986

[54] DISPOSABLE BLOOD PUMP

[75] Inventors: George P. Noon; Louis W. Feldman, both of Houston; Julia A. Peterson, South Houston, all of Tex.

[73] Assignee: Baylor College of Medicine, Houston, Tex.

[21] Appl. No.: 707,255

[22] Filed: Mar. 1, 1985

[51] Int. Cl.[4] .................. F04B 43/06; A61M 1/10
[52] U.S. Cl. .................. 417/394; 128/1 D; 128/DIG. 3; 604/153
[58] Field of Search ............ 417/394, 479; 128/1 D, 128/DIG. 3; 604/153, 4, 5, 6, 8

[56] References Cited

U.S. PATENT DOCUMENTS

| 3,127,846 | 4/1964 | Kerns | 604/153 |
| 3,639,084 | 2/1972 | Goldhaber | 128/1 D |
| 3,656,873 | 4/1972 | Schiff | 128/1 D |
| 3,974,825 | 8/1976 | Normann | 128/1 D |
| 3,995,774 | 12/1976 | Cooprider | 417/479 X |
| 4,144,595 | 3/1979 | Unger | 128/1 D X |
| 4,222,127 | 9/1980 | Donachy et al. | 128/1 D X |
| 4,360,324 | 11/1982 | O'Hara et al. | 417/394 X |
| 4,397,049 | 8/1983 | Robinson et al. | 128/1 D X |

FOREIGN PATENT DOCUMENTS 28996 3/1978 Japan .................. 128/1 D

*Primary Examiner*—Leonard E. Smith
*Attorney, Agent, or Firm*—Fulbright & Jaworski

[57] ABSTRACT

A hemocompatible flexible diaphragm and flexible wall pumping chamber positioned in a rigid body and actuated by alternating positive and negative fluid pulses. An inlet valve and an outlet valve are integrally molded in the pumping chamber. The diaphragm and pumping chamber are preferably molded of an elastomer. The pump is atraumatic, inexpensive and the pumping chamber and diaphragm are disposable.

3 Claims, 1 Drawing Figure

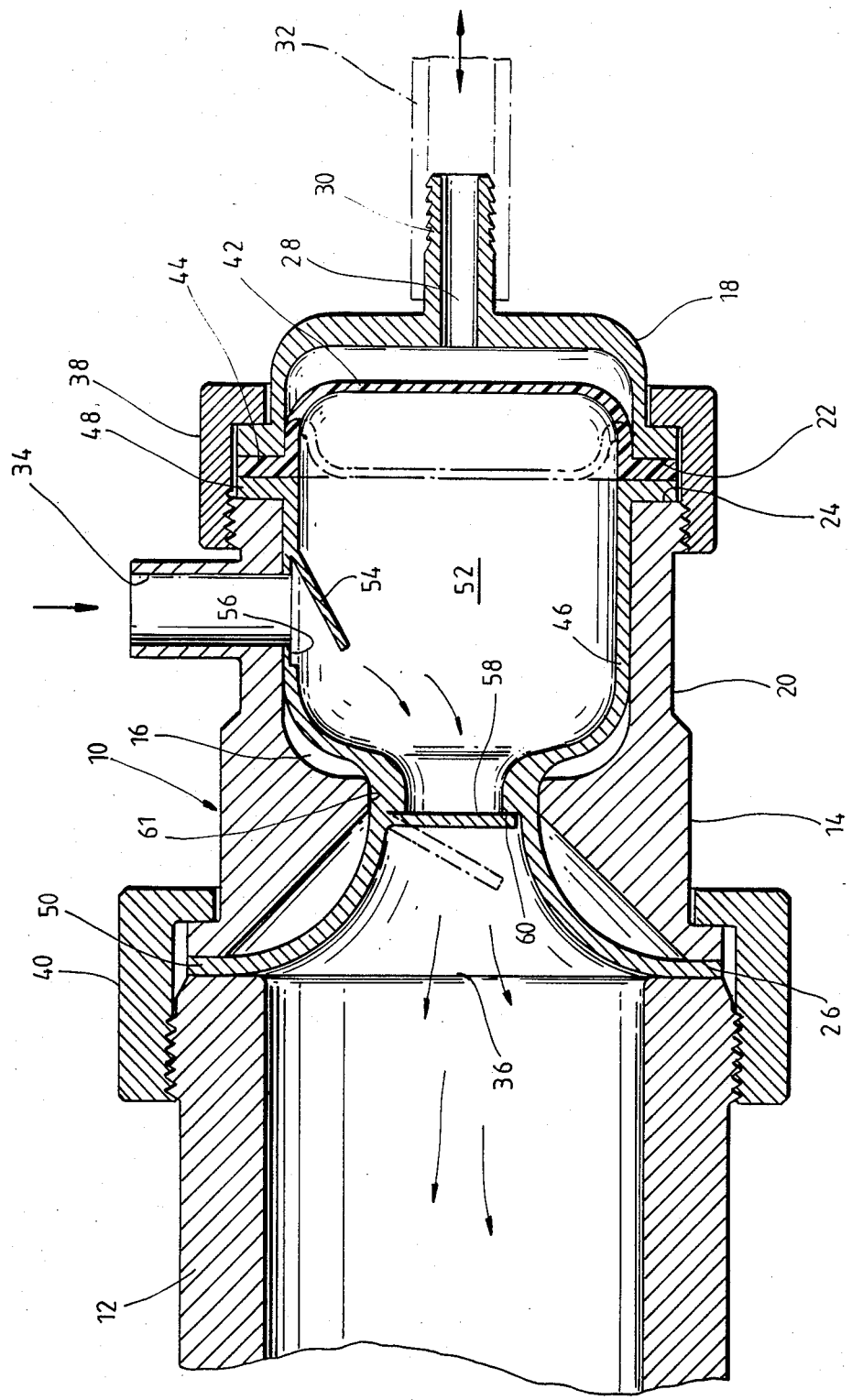

DISPOSABLE BLOOD PUMP

BACKGROUND OF THE INVENTION

It has been reported that approximately 360,000 open heart procedures were performed in 1983 and approximately 25 percent used a disposable membrane oxygenator. As open heart procedures become more complex, entailing higher risks, it is anticipated that membrane oxygenators will be utilized more often. The present invention is directed to an inexpensive, atraumatic, hemocompatible, pulsatile diaphragm pump that can be used for cardiopulmonary bypass and replace the conventional blood roller pump which after a time period causes blood trauma. The present pump, because of its qualities, is useful for use with membrane oxygenators. Present blood pumps are extremely expensive, use clinical heart valves which cost as much as $2,500 per valve, and still are thrombogenic. The present blood pump uses simple leaf valves that are integral in a pumping chamber and molded as part of the chambers to provide an inexpensive, disposable atraumatic pump which can be used for heart surgery, post operative support and other uses.

SUMMARY

The present invention is directed to a disposable blood pump and includes a rigid housing having a cavity therein and having first and second parts which are joined together with coupling means. A flexible hemocompatible diaphragm is positioned in the cavity and has an outer edge supported between the first and second housing parts. A flexible wall hemocompatible pumping chamber is positioned in the cavity having one end adjacent the diaphragm. The flexible chamber includes an integral inlet leaf valve and an integral outlet leaf valve with the inlet valve being in communication with a blood inlet port in the housing and the outlet valve being in communication with a blood outlet port in the housing. The valves are operable between open and close positions by alternating actuation of the diaphragm.

Still a further object of the present invention is the provision of a disposable blood pump including a rigid housing having a cavity therein and having first and second parts. The first part has a first supporting shoulder and the second part has a second and a third supporting shoulder. The first part includes a port for receiving actuating fluid and the second part includes a blood inlet port and a blood outlet port. Coupling means are connected between the first and second parts for joining the two parts with the first and second shoulders adjacent each other and coupling means are connected to the second part for joining the second part to an oxygenator. A flexible hemocompatible diaphragm is positioned in the cavity and the diaphragm includes an outer edge supported between the first and second supporting shoulders. A flexible wall hemocompatible pumping chamber having first and second ends is positioned in the cavity with the first end supported between the first and second supporting shoulders and the second end engaging the third shoulder. The chamber includes an integral inlet leaf valve and an integral outlet leaf valve, the inlet valve being in communication with the blood inlet port and the outlet valve being in communication with the blood outlet port and the valves being operable between open and close positions by alternating actuation of the diaphragm.

Still a further object of the present invention is wherein the second part of the body includes an inward projection for engaging the exterior of the chamber adjacent the outlet valve for supporting the outlet valve.

Still a further object of the present invention is the provision wherein the flexible diaphragm and chamber are of an elastomer material and molded to shape.

Other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

The drawing is an elevational view, in cross section, of the blood pump of the present invention connected to a membrane oxygenator.

DESCRIPTION OF THE PREFERRED EMBODIMENT

Referring now to the drawing, the reference numeral 10 generally indicates the disposable blood pump of the present invention which is useful in cardiac surgery such as cardiopulmonary bypass operations and which is particularly useful for connection to a membrane oxygenator 12. However, the pump 10 is useful in other applications such as a post operative support device.

The pump 10 includes a rigid housing 14 which may be any suitable material such as a rigid plastic or metal having a cavity 16 therein and includes a first part 18 and a second part 20. The first part 18 includes a first supporting shoulder 22 and the second part 20 includes a second supporting shoulder 24 and a third supporting shoulder 26. The first part 18 includes a port 28, preferably in the end, having suitable connecting means 30 for receiving an actuating fluid line 32 for receiving pneumatic or mechanical hydraulic created alternating actuating pulses. The second part 20 of the housing 14 includes a blood inlet port 34, preferably in a side, and a blood outlet port 36 at one end. Suitable coupling means such as a threaded nut 38 connects the first part 18 to the second part 20 of the body 14 and a connecting means such as a nut 40 is provided for connecting the second part 20 of the body 14 to any suitable blood handling or treating equipment such as a conventional membrane oxygenator.

A flexible hemocompatible diaphragm 42 is positioned in the cavity 16 of the body 14 having one side exposed to the port 28 and having an outer edge 44 which is supported between the first and second shoulders 22 and 24 of the parts 18 and 20 of the body 14. A flexible wall hemocompatible pumping chamber 46 is provided in the cavity 16 of the body 14 having a first end 48 and a second end 50. The first end 48 is positioned adjacent the diaphragm edge 44 and between the shoulders 22 and 24 of the parts 18 and 20 of the body 14 and the second end engages the third shoulder 26 for support between the body part 14 and the oxygenator 12. The edge 44 of the diaphragm and the ends 48 and 50 of the pumping chamber 46 are securely held in place by the units 38 and 40 for avoiding crevices which collect blood. The first end 48 is positioned adjacent the diaphragm 42 whereby pressure pulses generated by the diaphragm 42 will be transmitted to the interior 52 of the flexible wall chamber 46. The diaphragm provides a pulsatile actuation of the pump 10 which is less traumatic to blood as compared with the conventional roller pumps. The flexible wall chamber 46 includes an integral inlet leaf valve 54 and seat 56 and an integral outlet leaf valve 58 and a seat 60. The inlet valve 54 is in communication with the blood inlet port 34 and the outlet valve 58 is in communication with the outlet port 36. Both the diaphragm 42 and the flexible wall chamber 46 are molded members made of any suitable hemocompatible elastomer such as silicone rubber or urethane thereby providing a pumping action which is atraumatic to the blood supply. In addition, the diaphragm 42 and flexible wall chamber 46 with the integral valves 54 and 58 may be inexpensively made, and will thus allow the use of a pump for various applications including cardiac surgery which has not been available in the past because of the expense. The body 14 includes an inward projection 60 for engaging the exterior of the flexible chamber 46 adjacent and around the outlet valve 58 for securely supporting the outlet valve 58.

In one use, the pump 10 is generally connected, as noted, to an oxygenator 12 and the inlet port 34 is connected to the atrium of the patient and the actuating port 28 is connected to the line 32 leading to a pneumatic, hydraulic or mechanically actuated alternating pulse. When a negative pressure is applied to the actuating port 28, the parts are as shown in solid outline with the diaphragm 42 being drawn toward the actuating port 28, the inlet valve 54 being opened drawing blood into the interior 52 of the flexible wall chamber 46 while closing the outlet valve 58. And when the alternating positive pressure is applied in the port 28, the diaphragm 42 moves away from the port 28, closing the inlet valve 54, opening the outlet valve 58, and pumping blood from the interior 52 of the flexible wall chamber 46 out the outlet 36 to the oxygenator 12 and back to the patient, all as shown in dotted outline.

The pump 10 provides an inexpensive, disposable atraumatic pump which can be used in cardiac surgery, post operative support or other uses. After use, the diaphragm 42 and flexible wall chamber 46 may be discarded and replaced with new elements 42 and 46 for reuse, all at a minor expense compared to the expensive and still thrombogenic devices presently being used and will allow heart surgery to be performed in many cases not now available because of the expense.

The present invention, therefore, is well adapted to carry out the objects and attain the ends and advantages mentioned as well as others inherent therein. While a presently preferred embodiment of the invention has been given for the purpose of disclosure, numerous changes in the details of construction and arrangement of parts will be readily apparent to those skilled in the art and which are encompassed within the spirit of the invention and the scope of the appended claims.

What is claimed is:

1. A disposable blood pump comprising,
   a rigid housing having a cavity therein and having first and second parts, said first part having a first supporting shoulder and said second part having a second and third supporting shoulder,
   said first part including a port for receiving actuating fluid,
   said second part including a blood inlet port and a blood outlet port,
   coupling means connected between the first and second parts for joining said two parts with the first and second shoulders adjacent each other,
   coupling means connected to the second part for joining the second part to another blood handling device,
   a flexible hemocompatible diaphragm positioned in the cavity, said diaphragm having an outer edge supported between the first and second supporting shoulders,
   a flexible wall hemocompatible pumping chamber having first and second ends, and positioned in said cavity, said first end supported between the first and second supporting shoulders, said second end engaging said third shoulder,
   said chamber having an integral inlet leaf valve and an integral outlet leaf valve, said inlet valve being in communication with the blood inlet port, and said outlet valve being in communication with the blood outlet port, said valves being operable between open and closed positions by alternately actuating the diaphragm.

2. The apparatus of claim 1 wherein said second part of the body includes an inward projection for engaging the exterior of the chamber adjacent the outlet valve for supporting the outlet valve.

3. The apparatus of claim 3 wherein the flexible diaphragm and chamber are of an elastomer material and molded to shape.

* * * * *